(12) United States Patent
Yamauchi

(10) Patent No.: US 7,637,145 B2
(45) Date of Patent: Dec. 29, 2009

(54) GAS SENSOR FOR USE IN DETECTING CONCENTRATION OF GAS

(75) Inventor: Masanobu Yamauchi, Kariya (JP)

(73) Assignee: Denso Corporation, Kariya (JP)

( * ) Notice: Subject to any disclaimer, the term of this patent is extended or adjusted under 35 U.S.C. 154(b) by 0 days.

(21) Appl. No.: 11/937,714

(22) Filed: Nov. 9, 2007

(65) Prior Publication Data
US 2008/0134758 A1    Jun. 12, 2008

(30) Foreign Application Priority Data
Nov. 10, 2006  (JP) ............................ 2006-305659
Aug. 10, 2007  (JP) ............................ 2007-208966

(51) Int. Cl.
*G01N 9/00*  (2006.01)
(52) U.S. Cl. .................................................. 73/31.05
(58) Field of Classification Search ................. 73/31.05
See application file for complete search history.

(56) References Cited

U.S. PATENT DOCUMENTS

| | | | |
|---|---|---|---|
| 6,477,887 B1* | 11/2002 | Ozawa et al. | 73/31.05 |
| 6,637,256 B2* | 10/2003 | Shirai | 73/31.05 |
| 6,688,157 B2* | 2/2004 | Yamada et al. | 73/23.2 |
| 6,813,930 B2* | 11/2004 | Kimata et al. | 73/31.05 |
| 7,007,543 B2* | 3/2006 | Sakawa et al. | 73/23.32 |
| 7,472,578 B2* | 1/2009 | Yamauchi | 73/23.31 |
| 2007/0089486 A1* | 4/2007 | Yamauchi et al. | 73/31.05 |

FOREIGN PATENT DOCUMENTS

JP    2000-193629    7/2000

* cited by examiner

*Primary Examiner*—Hezron Williams
*Assistant Examiner*—Rodney T Frank
(74) *Attorney, Agent, or Firm*—Nixon & Vanderhye, PC

(57) ABSTRACT

A gas sensor comprises a sensing element detecting a gas concentration, a heater heating up the sensing element, an element-holding body holding the sensing element, and an atmosphere-side insulator. A pair of contact fittings is arranged between a base end part of the sensing element or the heater and an inner wall surface of the atmosphere-side insulator, and contacts a pair of electrodes disposed on the sensing element or the heater so as to press thereof. The contact fitting is provided with a base plate contacting the inner wall surface and an electrode contact member located to each of the electrodes and contacting the electrode. The gas sensor comprises suppressing means for suppressing the contact fittings from shifting relative to the electrodes in directions crossing the longitudinal direction. As an example, suppressing means are a plurality of fixing spring members pressing the inner wall surface from inside the insulator.

22 Claims, 10 Drawing Sheets

GAS SENSOR FOR USE IN DETECTING CONCENTRATION OF GAS

CROSS REFERENCE TO RELATED APPLICATIONS

The present application relates to and incorporates by reference Japanese Patent applications No. 2006-305659 filed on Nov. 10, 2006 and No. 2007-208966 filed on Aug. 10, 2007.

BACKGROUND OF THE INVENTION

1. Field of the Invention

The present invention relates to a gas sensor for detecting the concentration of a specific gas component contained in a gas to be measured.

2. Description of the Related Art

In most automobiles, exhaust systems are employed by internal combustion engines, in which the exhaust systems comprise a gas sensor disposed for measuring the concentration of a specific gas component contained in the exhaust gas. The gas component is oxygen, nitrogen oxides and others. One such an example of the gas sensor is set forth in Japanese Patent Laid-open (unexamined) No. 2000-193629, for example.

The gas sensor disclosed by this publication is illustrated in FIG. 1, in which a gas sensor 9 comprises an element-holding body 913 which allows a sensing element 910 to be inserted and held therein. The gas sensor 9 has a heater 911 for heating up the sensing element 910. An atmosphere-side insulator 914 is disposed at a base end part of the element-holding body 913 to cover a base end part of the sensing element 910 in the longitudinal (axial) direction thereof.

As shown in FIG. 1, between a base end part 912 of the heater 911 and an inner wall surface 941 of the atmosphere-side insulator 914, a pair of contact fittings 92 are arranged so as to be opposed to each other, in which the contact fittings 92 are in contact with a pair of electrodes 920 of the heater 911 in such a manner that the base end part of the heater 911 be compressed. Each of the contact fittings 92 comprises a base plate 921 abutted on the atmosphere-side insulator 914 and an electrode contact member 922 located in front of the base plate 921. Each electrode contact member 922 is in contact with each electrode 920 of the heater 911, so that the heater 911 is electrically connected to an externally provided electric power source.

However, in cases where the pair of contact fittings 92 hold the base end part 912 of the heater 911 under pressure as shown in FIG. 2, the contact fittings 92 occasionally causes a state in which the atmosphere-side insulator 914 and each electrode 920 come contact with each other at two points therebetween. For example, in cases where deformations such as warpage occurred at the base plate 921, the inner wall surface 941 of the atmosphere-side insulator 914 and the base plate 921 are point-contacted, which causes each contact fitting 92 to be supported at two point contacts.

When the gas sensor 9 receives vibration from the outside under such a two point contact state, with the contact points between each contact fitting 92 and the atmosphere-side insulator 914 and between each contact fitting 92 and each electrode 920 as rotating fulcrums, the contact fitting 92 may vibrate laterally so that the contact fitting 92 is deviated from a central axis direction S of the heater 911, as shown in FIG. 3. As a result, if such a case happens, a contacted part between the electrode contact member 922 and the electrode 920 is worn away, resulting in that it is difficult to keep stable electrical conductance therebetween.

SUMMARY OF THE INVENTION

The present invention has been completed with the above view in mind and has an object to provide a gas sensor whose contact fitting is prevented from vibrating laterally.

In order to achieve the object, as one aspect, the present invention provides a gas sensor comprising: a sensing element that detects a concentration of a specific gas component contained in a gas to be measured, the sensing element being elongated to have a longitudinal direction; a heater that heats up the sensing element for detection; an element-holding body that allows the sensing element to be inserted and to be held therein; an atmosphere-side insulator formed to have an inner wall surface and disposed to allow the inner wall surface to overlap with a base end part of either the sensing element or the heater in the longitudinal direction; a plurality of electrodes disposed on either the sensing element or the heater; a plurality of contact fittings disposed between the inner wall surface of the atmosphere-side insulator and the base end part of either the sensing element or the heater so as to contact the electrodes for electric conduction, respectively, wherein each of the contact fittings comprises a base plate located to contact the inner wall surface of the atmosphere-side insulator, an electrode contact member located to each of the electrodes, and a plurality of spring parts located to press the inner wall surface of the atmosphere-side insulator.

Each of the contact fittings comprises a plurality of fixing spring members each pressing the atmosphere-side insulator from its inner wall surface. Therefore, each contact fitting is able to contact the inner wall surface vie the fixing spring members at, at least, two contact points, and via a rear surface of the base plate at, at least, one contact point. Each contact fitting contacts each electrode of the sensing element or the heater via its electrode contact member at, at least, one contact point. In other words, each contact fitting is supported at, at least, four contact points between the sensing element or the electrode of the heater and the atmosphere-side insulator.

Thus, each contact fitting is well prevented from rotating laterally. Even if the gas sensor receives vibration from the outside, lateral vibration of each contact fitting is suppressed or prevented so that the contact fitting is not allowed to deviate from the central axial of the sensing element. It is possible to provide a gas sensor whose contact fitting is prevented from vibrating laterally. As a result, contacted portions of the electrodes of the sensing element or the heater with the electrode contact members are prevented from being worn away, thus increasing durability of the gas sensor. Additionally, a stable electrical continuance between the electrodes and the electrode contact members can be kept, giving a high reliability to the gas sensor.

In order to achieve the object, as another aspect, a gas sensor comprising: a sensing element that detects a concentration of a specific gas component contained in a gas to be measured, the sensing element being elongated to have a longitudinal direction; a heater that heats up the sensing element for detection; an element-holding body that allows the sensing element to be inserted and to be held therein, an atmosphere-side insulator formed to have an inner wall surface and disposed to allow the inner wall surface to overlap with a base end part of either the sensing element or the heater in the longitudinal direction; a plurality of electrodes disposed on either the sensing element or the heater; a plurality of contact fittings disposed between the inner wall surface of the atmosphere-side insulator and the base end part of either the sensing element or the heater so as to contact the electrodes for electric conduction, respectively, wherein each of the contact fittings comprises a base plate located to contact the inner wall surface of the atmosphere-side insulator and an electrode contact member located to each of the electrodes, wherein the base plate of each of the contact fittings comprises a rear surface that faces the inner wall surface of the atmosphere-side insulator and a concave portion recessed from the inner wall surface.

The base plate of each contact fitting has the concave portion recessed forward. Therefore, each contact fitting is in contact with the inner wall surface of the atmosphere-side insulator at, at least, two contact points, and is in contact with each electrode of the sensing element or the heater at, at least, one contact point. In other words, each contact fitting is supported at, at least, three contact points. As a result, each contact fitting can be prevented from vibrating laterally, thus obtaining similar advantages described in the foregoing aspect.

Additionally, each base plate has the concave portion, the base plate is enhanced in its strength, whereby deformation, such as warpage, of each contact fitting caused due to compressing the base end part of the sensing element or the heater can be restrained.

As another aspect, the present invention provides a gas sensor comprising: a sensing element that detects a concentration of a specific gas component contained in a gas to be measured, the sensing element being elongated to have a longitudinal direction; a heater that heats up the sensing element for detection; an element-holding body that allows the sensing element to be inserted and to be held therein; an atmosphere-side insulator formed to have an inner wall surface and disposed to allow the inner wall surface to overlap with a base end part of either the sensing element or the heater in the longitudinal direction; a plurality of electrodes disposed on either the sensing element or the heater; a plurality of contact fittings disposed between the inner wall surface of the atmosphere-side insulator and the base end part of either the sensing element or the heater so as to contact the electrodes for electric conduction, respectively, wherein each of the contact fittings comprises a base plate located to contact the inner wall surface of the atmosphere-side insulator and an electrode contact member located to each of the electrodes, wherein the base plate of each of the contact fittings comprises a rear surface that faces the inner wall surface of the atmosphere-side insulator and a plurality of convex portions projecting toward the inner wall surface.

The base plate of each contact fitting has the plurality of convex portions projecting on its rear surface. Therefore, each contact fitting is in contact with the inner wall surface of the atmosphere-side insulator at, at least, two contact points, and is in contact with each electrode of the sensing element or the heater at, at least, one contact point. In other words, each contact fitting is supported with at three or more points. As a result, each contact fitting can be prevented from vibrating laterally in a similar manner to the foregoing aspect, providing the same or similar advantages to those described.

Since the base plate has the convex portions, stiffness of the base plate is increased, enhancing durability against deformation, such as warpage, of the contact fitting.

Still as another aspect, the present invention provides a gas sensor comprising: a sensing element that detects a concentration of a specific gas component contained in a gas to be measured, the sensing element being elongated to have a longitudinal direction; a heater that heats up the sensing element for detection; an element-holding body that allows the sensing element to be inserted and to be held therein; an atmosphere-side insulator formed to have an inner wall surface and disposed to allow the inner wall surface to overlap with a base end part of either the sensing element or the heater in the longitudinal direction; a plurality of electrodes disposed on either the sensing element or the heater; a plurality of contact fittings disposed between the inner wall surface of the atmosphere-side insulator and the base end part of either the sensing element or the heater so as to contact the electrodes for electric conduction, respectively, wherein each of the contact fittings comprises a base plate located to contact the inner wall surface of the atmosphere-side insulator and an electrode contact member located to each of the electrodes, wherein the inner wall surface of the atmosphere-side insulator has a groove part recessed therefrom.

The inner wall surface of the atmosphere-side insulator has a groove part recessed from is surface, which allows each contact fitting to be in contact with the inner wall surface at, at least two contact points. Each contact fitting is also able to keep at least one contact point with the electrode, thus securing at least three contact points between each electrode of the sensing element or the heater and the atmosphere-side insulator. Even if deformation such as warpage is caused, each contact fitting is prevented from vibrating laterally, also providing similar advantages to the foregoing ones.

In the present invention, an A/F (air/fuel) sensor, an $O_2$ sensor, an $NO_x$ sensor and others can be quoted as the gas sensor. In addition, the sensing element according to the present invention may be of a laminated type of sensing element or a cylindrical bottomed cup-shaped sensing element.

In cases where the sensing element is a limited type of sensing element, the sensing element and the heater are formed integrally with each other. Further in this case, the element-holding body may be configured with an element-side insulator which enables the sensing element to be inserted and held therein and a metallic housing which enables this element-side insulator to be inserted and held therein.

On the other hand, when the cylindrical bottomed cup-shaped sensing element is used, the element-holding body may be a metallic housing which allows the sensing element to be inserted and held directly inside this metallic housing.

It is preferred that the base plate of each of the contact fittings comprises a rear surface that faces the inner wall surface of the atmosphere-side insulator and a concave portion recessed from the inner wall surface. It is also preferred that the base plate of each of the contact fittings comprises a rear surface that faces the inner wall surface of the atmosphere-side insulator and a plurality of convex portions projecting toward the inner wall surface.

It is preferred that each of the fixing spring members comprises a bent portion formed as a convex oriented toward a base end of the sensing element by bending part of the base plate toward the sensing element and a folded end extending from the bent portion toward the distal end of the sensing element and forcibly pressing the inner wall surface of the atmosphere-side insulator.

According to this configuration, a middle part of the bent portion in the radial direction of the censing element gives a fulcrum to the bent portion as to an elastic force generated therefrom. Thus the fulcrum is positioned in an almost radially middle range in a space where the rear surface of the base plate and the folded end of each fixing spring member contact the inner wall surface of the atmosphere-side insulator. In addition, since the fixing spring members are formed as a convex oriented toward a base end of the sensing element. These configurations make it possible that a distance between a distal edge of the base plate, which is located on the distal end side of the gas sensor, and each folded end is made larger, thus providing a stable arrangement of the contact fittings in the atmosphere-side insulator. Such an arrangement leads to sufficiently suppressing a base-side end portion of each contact-fitting from tilting forward within the atmosphere-side insulator, that is, toward the central axis of the gas sensor.

In the above arrangement, it is also preferable that, when a distance between a distal edge of the base plate, which is on the opposite side to the bent portion, and a tip of the folded end in the longitudinal direction is expressed as "A" and a distance between the distal edge of the base plate and a middle part of the bent portion in the longitudinal direction is expressed as "B," a relationship of "A≧0.5B" is met. This means the distance "A" can be made fully larger, further enhancing the foregoing stable arrangement.

It is also preferred that the electrodes comprises a pair of electrodes disposed on the base end part of either the sensing element or the heater and the contact fittings comprises a pair of contact fittings that contact the pair of electrodes, respectively, such that the pair of the contact fittings forcibly pinch the base end part of either the sensing element or the heater. In this structure, the pair of electrodes can be strongly pinched the pair of the contact fittings, which secures a stable electric conduction between the electrodes and the fittings in an easier manner.

DETAILED DESCRIPTION OF PREFERRED EMBODIMENTS

Various embodiments of a gas sensor according to the present invention will now be described with reference to the accompanying drawings.

In the following embodiments and modifications, as denoted in FIG. 4, a side on which the gas sensor is inserted into an exhaust pipe or other devices is referred to as a "distal end side" or "distal side," while the opposite side thereto is referred to as a "base end side" or "base side." In addition, as to the contact fitting, an approaching direction to the central axis "S" of the gas sensor is referred to as a "forward (in the radial direction around the central axis S of the gas sensor)," and the opposite direction thereto is referred to as a "backward (in the radial direction of the gas sensor)."

First Embodiment

Referring to FIGS. 4-8, a first embodiment of a gas sensor will now be described.

Figure 1:
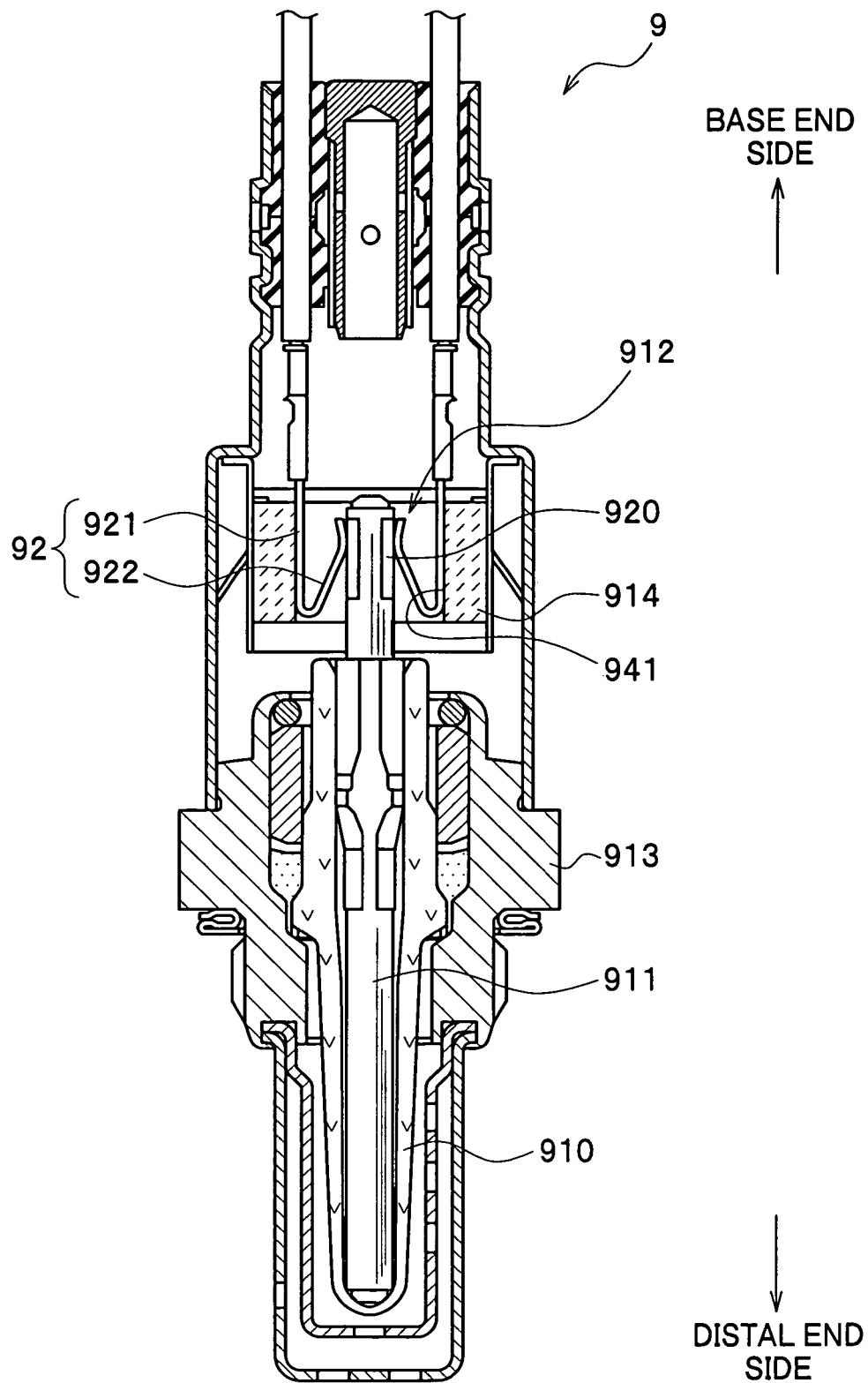
FIG. 1 is an axial (longitudinal) sectional view showing a conventional gas sensor.
Figure 2:
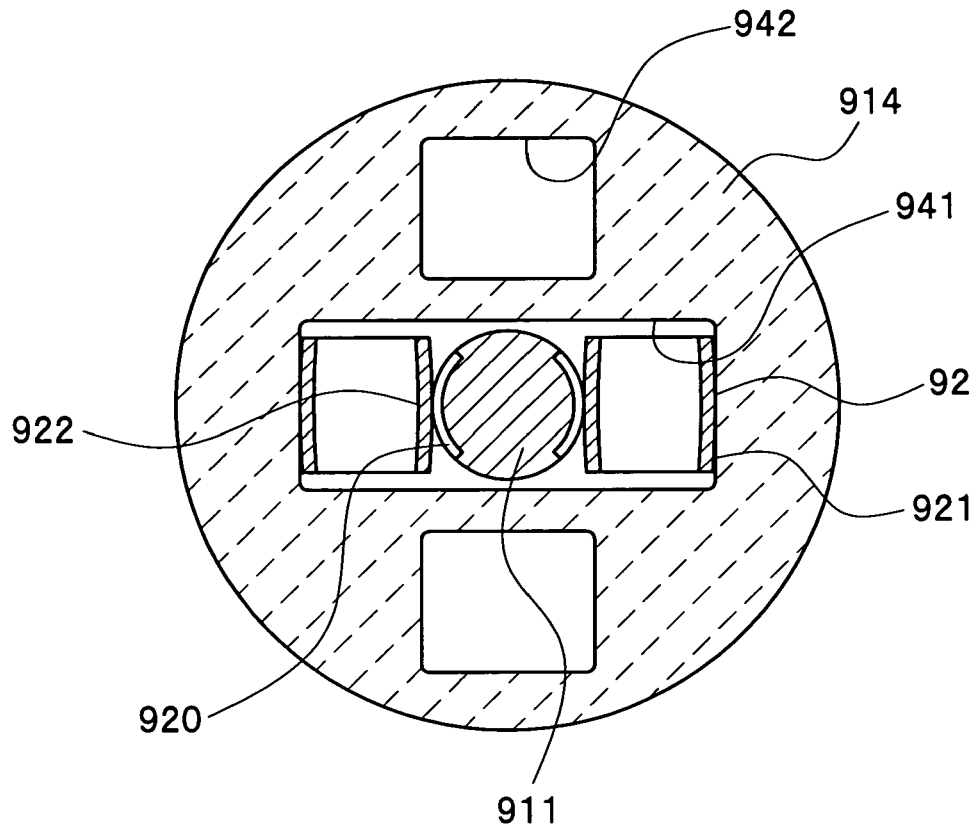
FIG. 2 is a sectional view showing an atmosphere-side insulator and contact fittings of the conventional gas sensor shown in FIG. 1.
Figure 3:
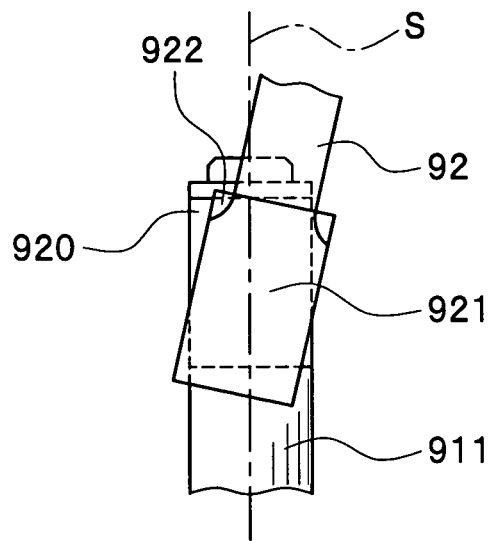
FIG. 3 partially illustrates a state in which lateral vibration occurs to a contact fitting in the conventional gas sensor shown in FIG. 1.
Figure 4:
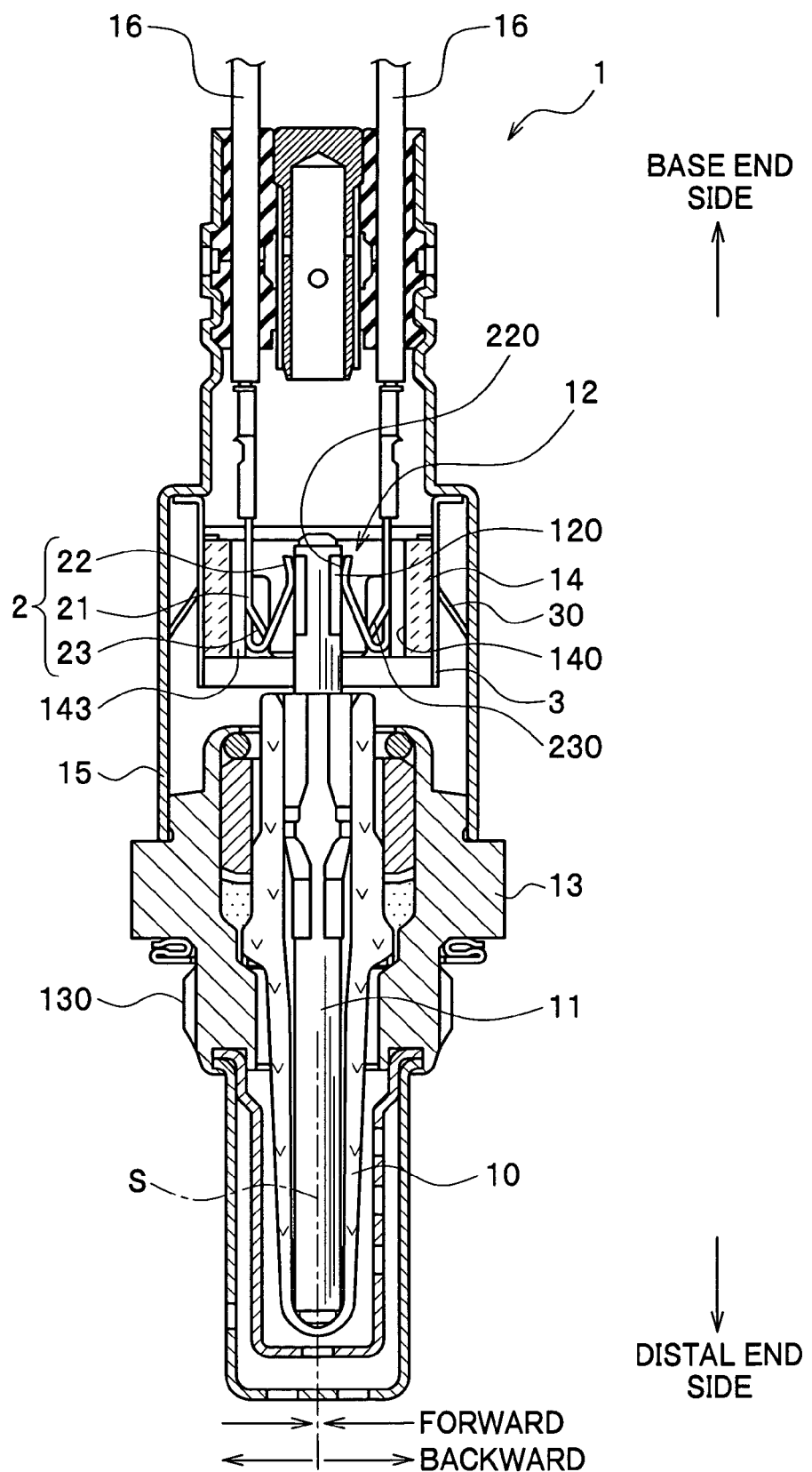
FIG. 4 is an axial sectional view showing a gas sensor according to a first embodiment of the present invention.

As shown in FIG. 4, a gas sensor 1 according to the present embodiment is provided. The gas sensor 1 comprises a sensing element 10 that detects the concentration of a specific gas component contained in a gas to be measured, a heater 11 that heats up the sensing element 10, an element-holding body 13 that allows the sensing element 10 to be inserted and held therein, and an atmosphere-side insulator 14 disposed at a base end part of the element-holding body 13 to cover a base end part of the sensing element 10 in the longitudinal direction along the central axis S.

Figure 5:
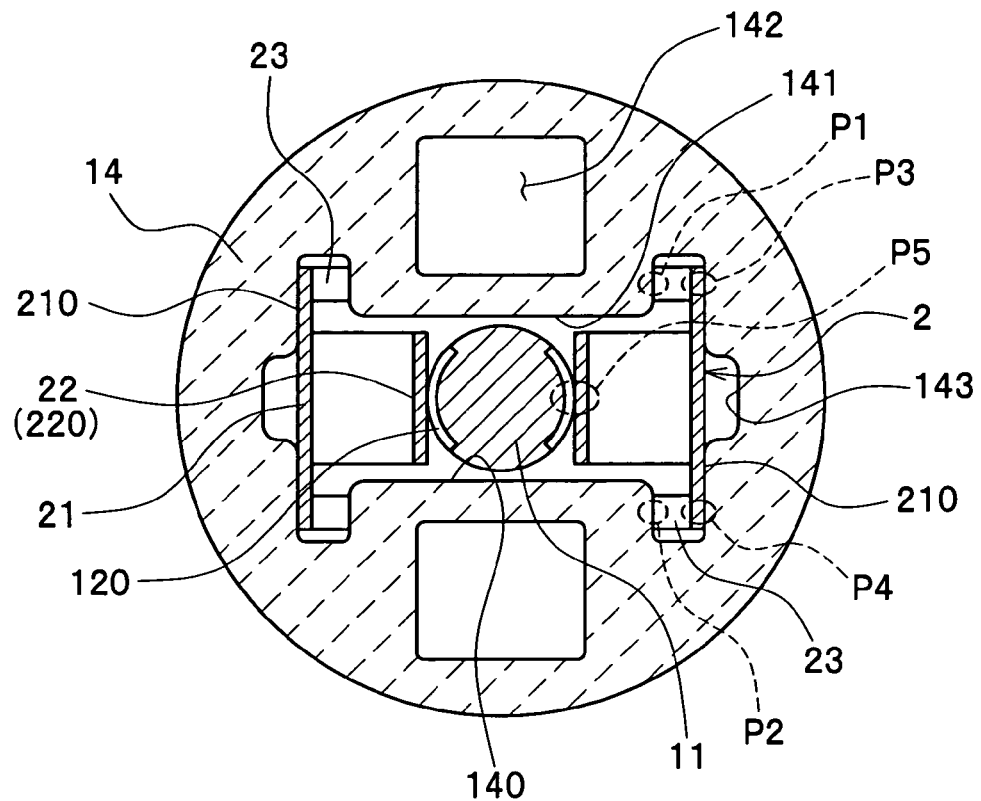
FIG. 5 is a sectional view, taken along a planar direction perpendicular to a longitudinal direction of a sensing element, showing an atmosphere-side insulator and contact fittings of the gas sensor of the first embodiment.
Figure 6:
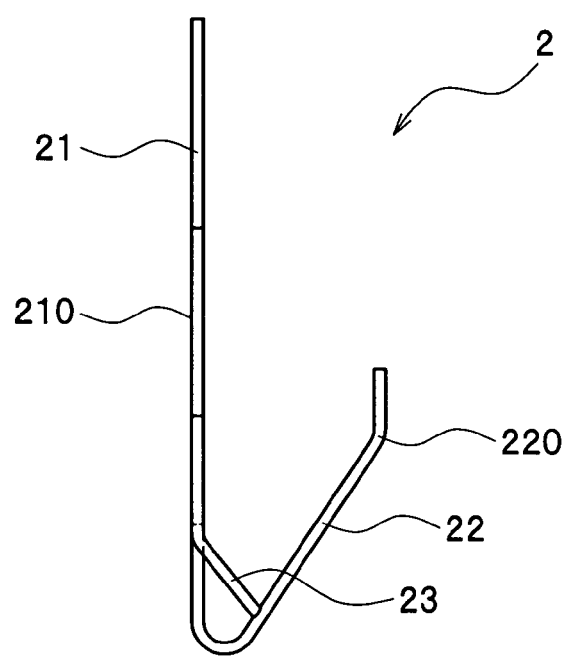
FIG. 6 is a side view showing a contact fitting employed in the first embodiment.

As shown in FIGS. 4 and 5, between a base end part 12 of the heater 11 and an inner wall surface 140 of the atmosphere-side insulator 14, a pair of contact fittings 2 are arranged to be faced to each other. The fittings 2 are in contact with a pair of electrodes 120 of the heater 11 respectively to compress the base end part of the heater 11.

As shown in FIGS. 4-7, each of the contact fittings 2 is formed for example into a single member comprising a base plate 21 abutted on the inner wall surface 140 of the atmosphere-side insulator 14, an electrode contact member 22 located in front of the base plate 21 in the forward direction, and a pair of fixing spring members 23 for pressing the atmosphere-side insulator 14 from the inside thereof, that is, from the inner wall surface 140.

Figure 7:
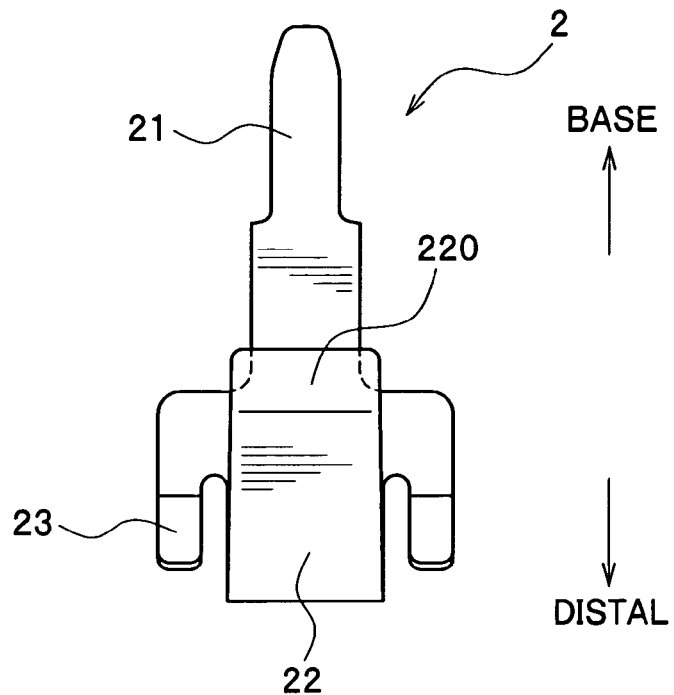
FIG. 7 is an elevation view showing the contact fitting shown in FIG. 6.

As shown in FIG. 7, the base plate 21 of each contact fitting 2 is formed in a tiered shape so that its widthz becomes graduallyz narrower toward the base end side.

As shown in FIGS. 4-7, each of the electrode contact members 22 is formed by folding back the distal end of the base plate 21 toward its base end part. The electrode contact member 22 has a bent part 220 directed toward the base plate 21 and made to contact each electrode 120 of the heater 11.

As shown in FIGS. 5 and 7, each of the fixing spring members 23 is located on both sides of the base plate 21 in the width direction of the base plate 21.

As shown in FIGS. 4-7, the fixing spring member 23 is formed by bending part of the base plate 21 to be oblique from the base plate 21 and located in the atmosphere-side insulator 14 to be oriented forward. The fixing spring member 23 arranged in the inner wall surface 140 presses the atmosphere-side Insulator 14 from the inside thereof. As a reaction of the pressing action, a rear surface 210 of the base plate 21 pushes back the inner wall surface 140 of the atmosphere-side insulator 14.

Figure 8:
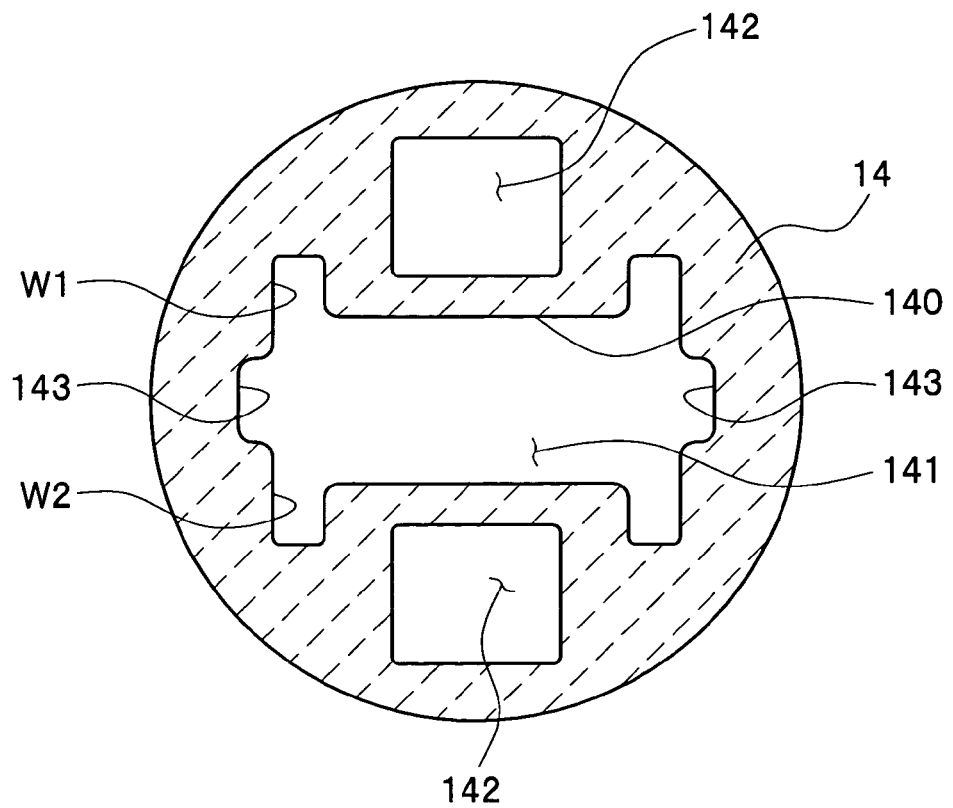
FIG. 8 is a sectional view, taken along the planar direction, showing the atmosphere-side insulator.

As shown in FIGS. 4, 5 and 8, part of the inner wall surface 140 of the atmosphere-side insulator 14, which is located at the back of the base plate 21, has a groove 143 formed to be recessed backward. Therefore, the rear surface 210 of the base plate 21 forcibly comes into contact with both wall portions W1 and W2 of the inner wall surface 140 which are separated by the groove 143.

As shown in FIG. 4, the atmosphere-side insulator 14 is maintained by a cylindrical holder 3. Between an atmosphere-side cover 15 and the holder 3, an external spring 30 is disposed. The external spring 30 expands and contracts so that the atmosphere-side insulator 14 can be fixed to and maintained at the predetermined position in the cover 15.

The groove 143 is formed to run in the axial (longitudinal) direction of the sensor and is one in number. This groove 143 is located at a position opposed to a central position of the rear surface 210 of each of the contact fittings 2 in a planar direction of the base plate 21.

Further, as shown in FIG. 5, between the atmosphere-side insulator 14 and the heater 11, each contact fitting 2 is in contact with the atmosphere-side insulator 14 and the heater 11 at five contact points among those members 14, 11 and 2. In other words, each contact fitting 2 is in contact with the inner wall surface 140 of the atmosphere-side insulator 14 via its fixing spring members 23 (i.e., contact at two contact points P1 and P2 as shown in FIG. 5) and via the rear surface 210 of the base plate 21 (i.e., contact at two contact points P3 and P4 shown in FIG. 5). In addition, each contact fitting 2 contacts each electrode 120 of the heater 11 via its electrode contact member 22 (i.e., contact at one contact point P5 shown in FIG. 5). Thus, in all, the contacting operations at five contact points are secured.

The number of contact points at each contact location increases, if there are irregularities on the surface to be contacted at each contact location. In the present description, the term "contact point" is used to mean only a position at which the contact is made regardless of largeness in area to be contacted. The term therefore "contact point" includes a "contact area."

As shown in FIG. 4, the electrodes 120 of the heater 11 are electrically connected to a pair of lead wires 16 for the heater, electrodes of the sensing element 10 (not shown in FIG. 4) are also electrically connected to a pair of lead wires for sensing (not shown in FIG. 4).

Further, as shown in FIGS. 5 and 8, the atmosphere-side insulator 14 comprises a first through-bore 141 passing through the axial direction at an approximately center of the section and two second through-bores 142 on both sides of the first through-bore 141. The pair of lead wires 16 for the heater is inserted through the first through-bore 141, while the lead wires for sensing (not shown) are inserted through the second through-bores 142.

As shown in FIG. 4, the sensing element 10 of the present embodiment is formed as a cylindrical bottomed cup-shaped sensing element. This sensing element 10 has a base end part at which a pair of terminal portions for sensing (not shown in FIG. 4) is provided to be electrically connected to the foregoing two lead wires for sensing, though not shown.

As illustrated in FIGS. 4 and 5, the heater 11 is formed as a columnar heater disposed inside the cup-shaped sensing element 10. As described above, the pair of contact fittings 2 and the heater 11 is made to be in contact with each other via the electrodes 120, disposed at the base end part 12 of the heater 11, and the bent part 220 of each of the electrode contact members 22. Thus, the contact fittings 2 are electrically continued to an external electric power source through the foregoing lead wires 16 for the heater.

The element-holding body 13 consists of a metallic housing. The housing has a screw portion 130 formed at a distal end thereof and threaded and fastened to an exhaust pipe to be sensed (not shown). For example, when external vibration transmits to the exhaust pipe, the vibration is obliged to transmit to the inside of the gas sensor 1 through the housing. As a result, the vibration finally transmits to the contact fittings 2.

The operations and effects of the present embodiment will now be described.

As described, each of the contact fittings 2 comprises a plurality of fixing spring members 23 pressing the inner wall surface 140 of the atmosphere-side insulator 14. Therefore, each contact fitting 2 contacts the inner wall surface 140 via its fixing spring members 23 at two contact points and via the rear surface 210 of the base plate 21 at one contact point, and contacts the electrode 120 of the heater 11 via the electrode contact member 22 at one contact point. In other words, each contact fitting 2 is supported at four contact points between the atmosphere-side insulator 14 and each of the electrodes 120 of the heater 11.

In this way, the contact points (areas) serving as supporting points (areas) that support each contact fitting 2 against vibration are increased in number and, at the same time, spread two- and three-dimensionally, compared to the conventional. That is, each of the contact fittings 2 is supported more intensively at the four contact points, with the result that each contact fitting 2 is prevented from rotating relative to the heater 11. Therefore, even if the gas sensor 1 receives vibration from the outside, the contact fittings 2 are prevented or suppressing from vibrating laterally, avoiding deviation of the contact fittings 2 from the central axis of the sensing element 10.

In addition, the contact parts of the electrodes 120 of the heater 11, which contact parts are in contact with the electrode contact member 22, are also prevented from being worn away. Further, a stable electric conduction between the electrodes 120 of the heater 11 and the electrode contact member 22 can be kept.

As shown in FIGS. 4 and 5, the inner wall surface 140 of the atmosphere-side insulator 14, which inner wall surface contacts the rear surface 210 of the base plate 21, has the groove 143 recessed backward. It is thus possible that the contact fittings 2 are prevented from vibrating laterally more reliably.

Furthermore, between the base end part 12 of the heater 11 and the inner wall surface 140 of the atmosphere-side insulator 140, the pair of the contact fittings 2 comes into contact with the pair of electrodes 120, respectively. Thus the pair of contact fittings 2 is able to strongly and elastically pinch the electrodes 120 disposed on the heater 11, thus easily securing a stable electric conduction between the electrodes 120 and the fittings 22.

As described above, according to the present embodiment, it is possible to provide a gas sensor whose contact fittings are prevented from vibrating laterally in a steadier manner.

Second Embodiment

Figure 9:
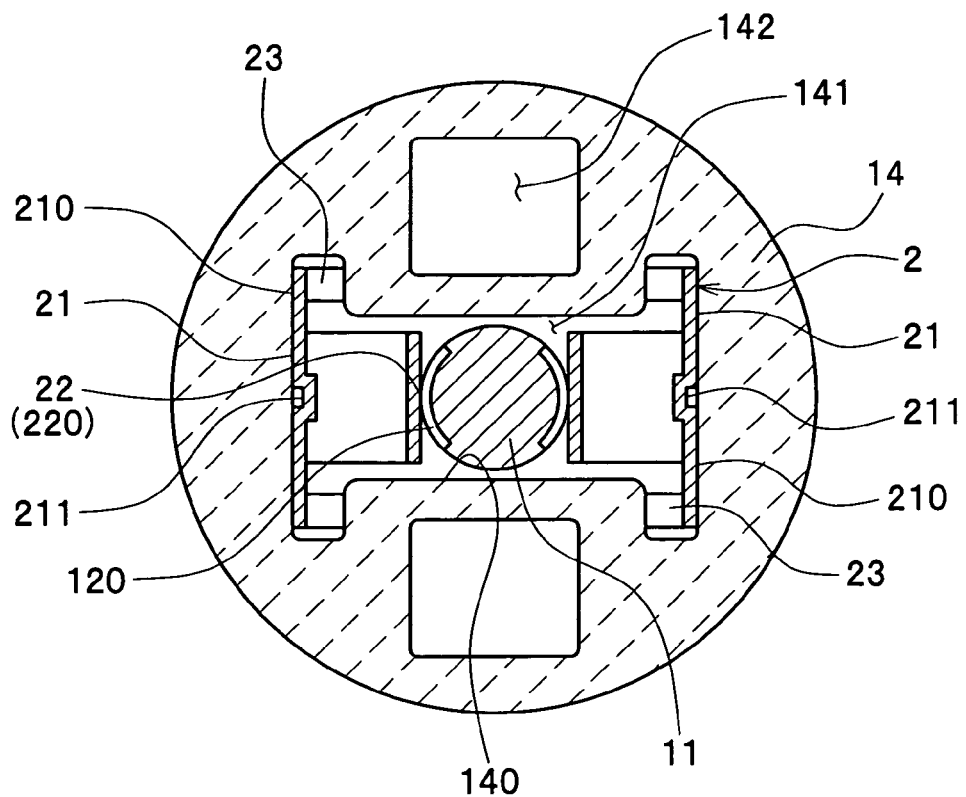
FIG. 9 is a sectional view, taken along the planar direction, showing an atmosphere-side insulator and contact fittings according to a second embodiment of the present invention.
Figure 10:
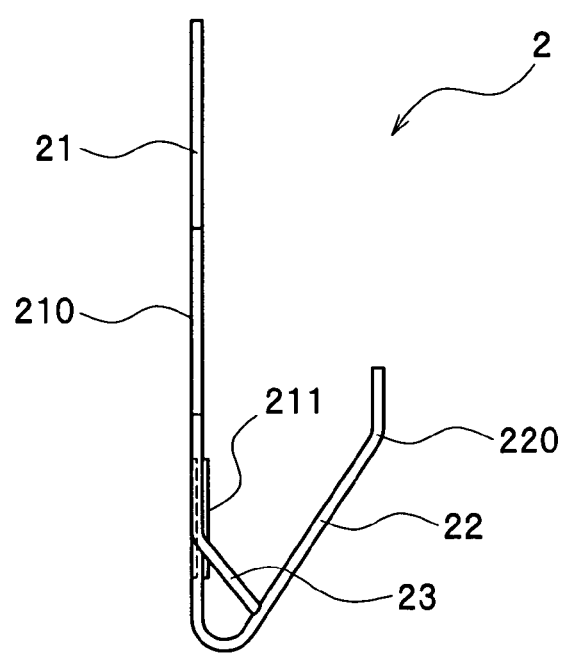
FIG. 10 is a side view showing a contact fitting employed in the second embodiment.
Figure 11:
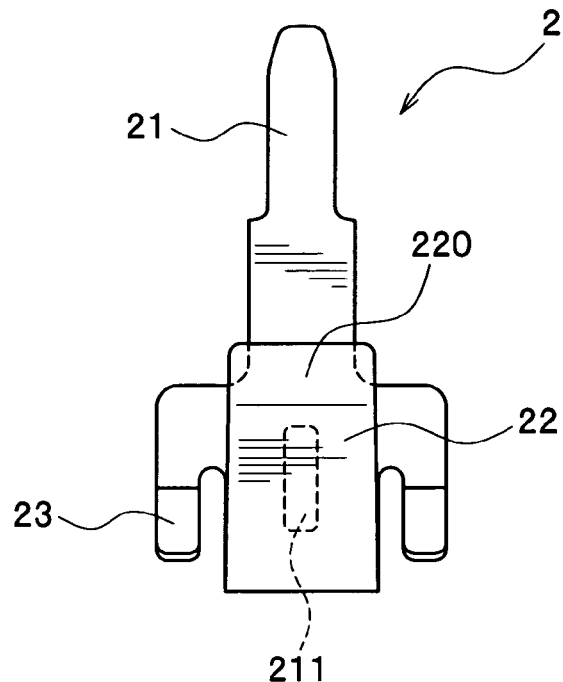
FIG. 11 is an elevation view showing the contact fitting shown in FIG. 10.

As shown in FIGS. 9-11, a second embodiment of the present invention will now be described.

In the second embodiment, the same or identical components as or to those described in the first embodiment are given the same reference numerals as those in the first embodiment for the sake of simplified explanation. This explanation manner is also true of the succeeding embodiments and modifications therefrom.

The second embodiment shows, by way of example, a gas sensor 1 in which the base plate 21 of each contact fitting 2 has a concave portion 211 recessed from the rear surface 210 of the base plate, as shown in FIGS. 9-11. Each of the contact fittings 2 comprises a pair of fixing spring members 23 pressing the inner wall surface 140 of the atmosphere-side insulator 14. Instated of forming such a concave portion 211, the inner wall surface 140 has no groove which can be seen in FIG. 5 (refer to the grooves 143).

As shown in FIG. 9, each contact fitting 2 is in contact with the inner wall surface 140 of the atmosphere-side insulator 14 via the fixing spring members 23 at two contact points, and via the rear surface 210 of the base plate 21 at two contact points, because the concave portion 211 divides the contact portion based on the rear surface 210. Furthermore, each contact fitting 2 is contact with the electrode 120 of the heater 11 via its electrode contact member 22 at one contact point. In other words, each contact fitting 2 is in contact with both the atmosphere-side insulator 14 and the heater 11 using the five contact points. Therefore, similarly to the structure explained in the first embodiment, the contact fittings 2 are well prevented from vibrating laterally. Since the base plate 21 has the concave portion 211 to raise stiffness of the base plate 21, whereby deformation of the contact fittings 2, such as warpage, which is due to compressing the base end part 12 of the heater 11 can be restrained.

Third Embodiment

Figure 12:
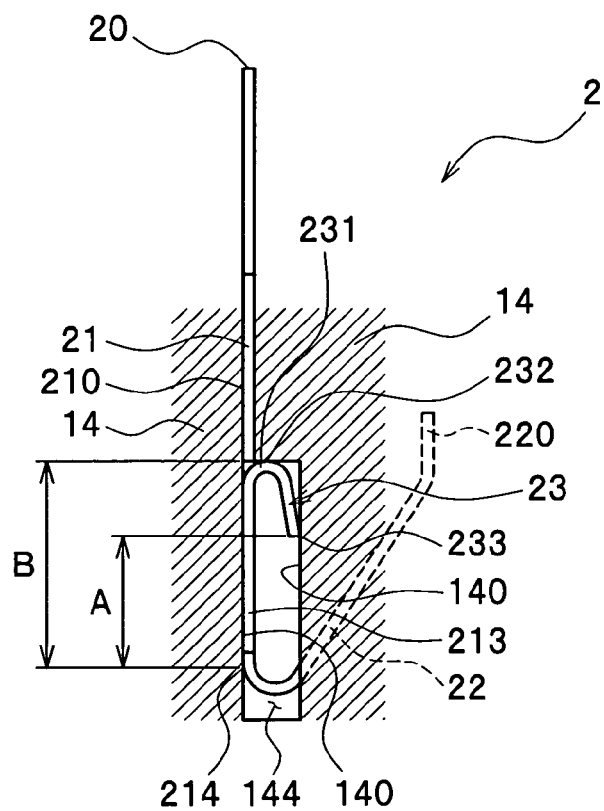
FIG. 12 is a side view showing a contact fitting employed in a third embodiment of the present invention.
Figure 13:
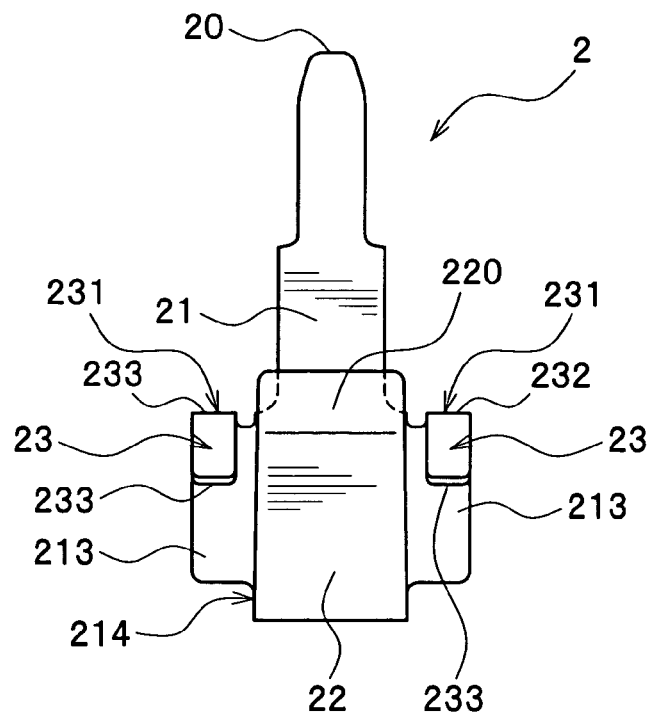
FIG. 13 is an elevation view showing the contact fitting shown in FIG. 12.

Referring to FIGS. 12 and 13, a third embodiment will now be described. A gas sensor 1 according to the present embodiment employs the fixing spring members 23 bent to be convex toward the base end part, as shown in FIGS. 12 and 13.

Specifically, each of the fixing spring members 23 comprises a bent portion 231 and a folded distal portion 233. The bent portion 231 is formed by bending a base-end-side end portion of a side plate portion 213 so that the base-end-side end portion becomes convex so as to be oriented toward the base end side. The side plate portion 213 is formed integrally with each of both lateral ends of the base plate 21 and is formed by extending the base plate 21 outward in the lateral direction thereof. The folded end 233 is thus directed toward the distal end side from the bent portion 231. Hence, when the contact fitting 2 is viewed along its side-viewing direction (i.e., along a planar direction of the base plate 21), each of the fixing spring members 23 has a convex bent attitute (i.e., an almost U-shaped attitude) toward the base end part, as shown in FIG. 12.

The folded end 233 is therefore located to forcibly press the inner wall surface 140 of the atmosphere-side insulator 14.

In particular, in the present embodiment, an approximately middle part of the bent portion 231 in the radial direction gives each fixing spring member 23 a fulcrum 232 on which an elastic force is generated by each fixing spring member 23. As shown in FIG. 12, the fulcrum 232 is thus located in an almost central range of a spring accommodating space 144 in the radial direction, in which the spring accommodating space 144 is formed between both inner wall surfaces 140 of the atmosphere-side insulator 14, the inner wall surfaces 140 of which receives contacts of both the rear surface 210 of the base plate 21 and the folded ends 233 of the fixing spring members 23, respectively. Thus the fulcrum 232 of each fixing spring member 23 is positioned forward than the base plate 21. In addition, the fixing spring members 23, which is ahead of the bent portions 231, are oblique to the base plate 21.

Moreover, the base plate has a distal end 214, which is fully separated form the folded ends 233 in the axial direction along the axis S of the sensing element, as shown in FIG. 12. The distal end 144 is defined as a distal-most edge of the base plate 21 which still comes in contact with the inner wall surface 140 of the atmosphere-side insulator 14, as shown in FIG. 12.

When distances are given such that an axial distance between the distal end 214 and the folded ends 233 is "A" and an axial distance between the distal end 214 and the middle part (i.e., the position providing the fulcrum 232) of each of the bent portions 231 is "B," a relationship between the distances "A" and "B" is set to be "A is equal to or larger than 50% of B (A≧0.5B)." Additionally, the axial distance "A" can be as larger as possible, so long as the fixing spring members 23 can be produced in the space 144.

As stated, in the present embodiment, the approximate middle part of each bent portion 231 gives the fulcrum 232 to each fixing spring member 23 for generating the elastic force, and the fulcrum 232 is located at the approximate center of the spring accommodating space 144 in the radial direction. Furthermore, the fixing spring members 23 are bent at the base-side ends of the side plate portions 213 as described. All these geometries make it possible to give a larger amount to the axial distance "A" between the distal end 214 of the base plate 21 and the folded ends 233. Especially, since the relationship of A≧0.5B is kept in this embodiment, the contact fitting 2 can be mounted in the atmosphere-side insulator 14 in a sufficiently stable manner.

Accordingly, a base end portion 20 of the contact fitting 2 can fully be suppressed from tilting forward in the atmosphere-side insulator 14. In addition to this advantage, the structure of the present embodiment is able to gain similar advantages to those stated in the first embodiment.

Fourth Embodiment

Figure 14:
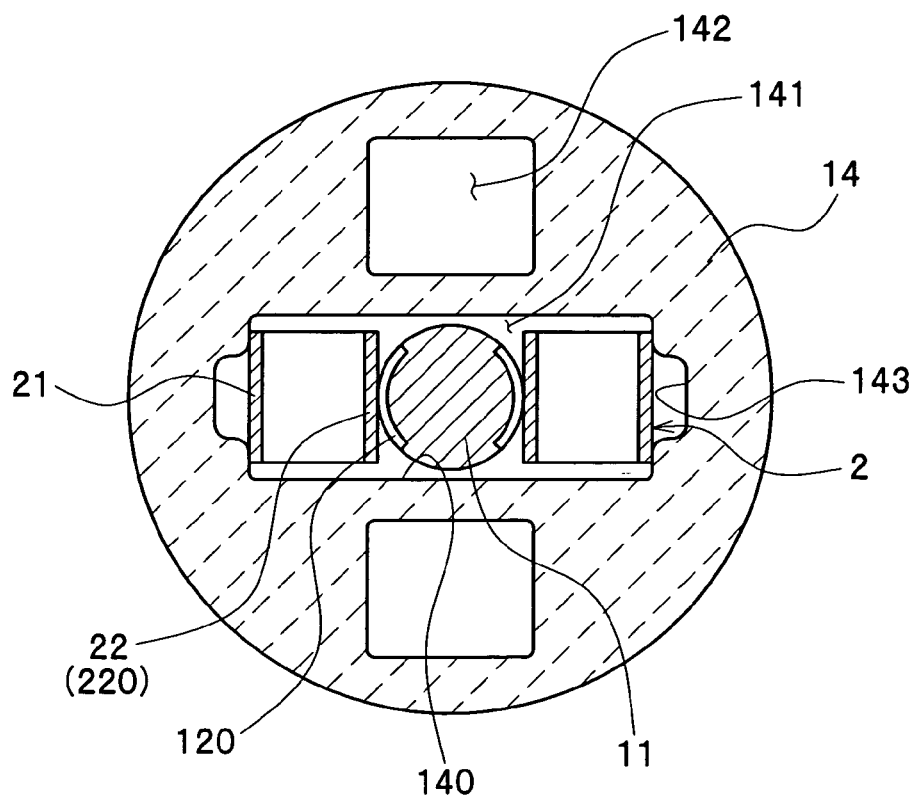
FIG. 14 is a sectional view, taken along the planar direction, showing an atmosphere-side insulator and contact fittings according to a fourth embodiment of the present invention.

Referring to FIG. 14, a fourth embodiment of the present invention will now be described.

As shown in FIG. 14, the present embodiment shows, by way of example, the gas sensor 1 in which the atmosphere-side insulator 14 has an inner wall surface 140 with grooves 143 recessed backward from the surface. The contact fitting 2 has no fixing spring member which has been described in the first embodiment and the rear surface of the base plate 21 of each contact fitting 2 has no concave portion which has been described in the second embodiment.

As shown in FIG. 14, each of the contact fittings 2 is in contact with the inner wall surface 140 of the atmosphere-side insulator 14 via both edges of the groove 143 and the rear surface of the base plate 21 at two contact points. Moreover each contact fitting 2 is in contact with the electrode 120 of the heater 11 via each electrode contact member 22 at one contact point. Hence, even if deformation such as warpage is caused, each contact fitting 2 is prevented from vibrating laterally, thereby providing similar advantages to those gained in the first embodiment.

Fifth Embodiment

Figure 15:
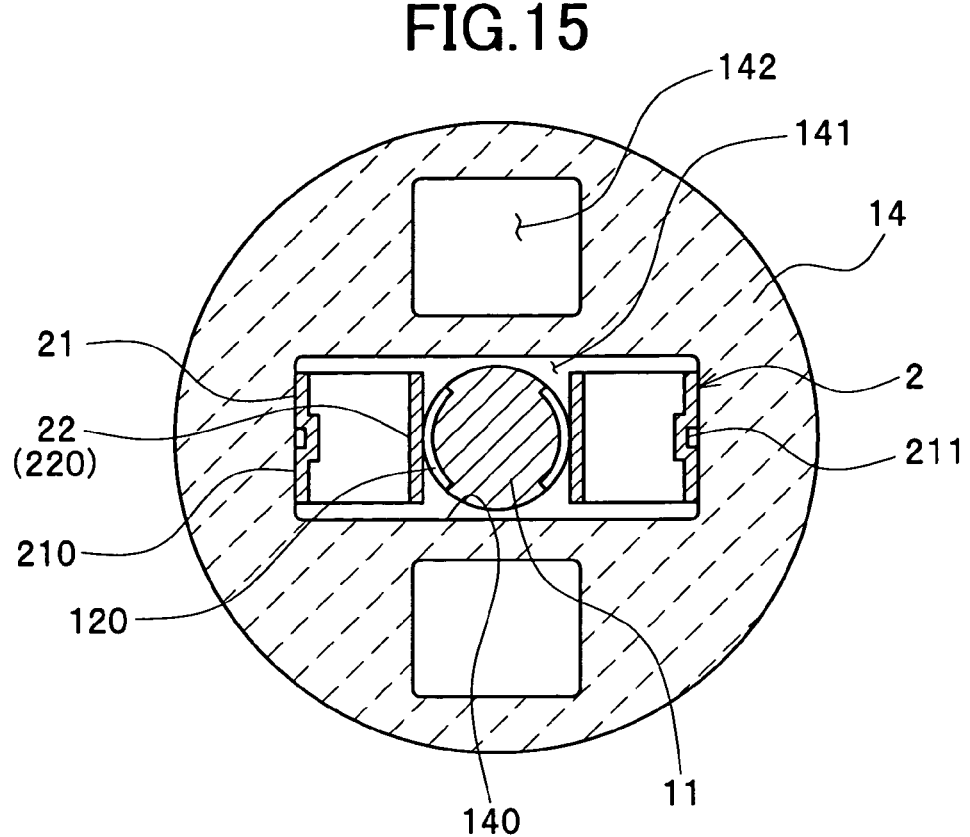
FIG. 15 is a sectional view, taken along the planar direction, showing an atmosphere-side insulator and contact fittings according to a fifth embodiment of the present invention.

Referring to FIG. 15, a fifth embodiment of the present invention will now be described.

As shown in FIG. 15, the present embodiment shows, by way of example, a gas sensor 1 whose base plate 21 has a concave portion 211 recessed forward on the rear surface 210 of the base plate 21. Instead of this, the contact fittings 2 and the atmosphere-side insulator 14 are simplified in their structures such that the contact fittings 2 have no fixing spring members on both sides of the base plate 21 and the inner wall surface 140 of the atmosphere-side insulator 14 has no groove.

As shown in FIG. 15, each contact fitting 2 is in contact with the inner wall surface 140 of the atmosphere-side insulator 14 via both plate portions of the base plate 21 which are separated by the concave portion 211 at two contact points. Further, each contact fitting 2 is in contact with the electrode 120 of the heater 11 via each electrode contact member 22 at one contact point. Hence, the contact fitting 2 is prevented from vibrating laterally based on similar supports mentioned in the first embodiment.

Moreover, since the base plate 21 has the concave portion 211, strength of the base plate 21 is increased, whereby it can be restrained that deformation such as warpage of the contact fittings 2 caused due to compressing the base end part 12 of the heater 11. The remaining advantages stated in the first embodiment can also be obtained in the present embodiment.

Sixth Embodiment

Figure 16:
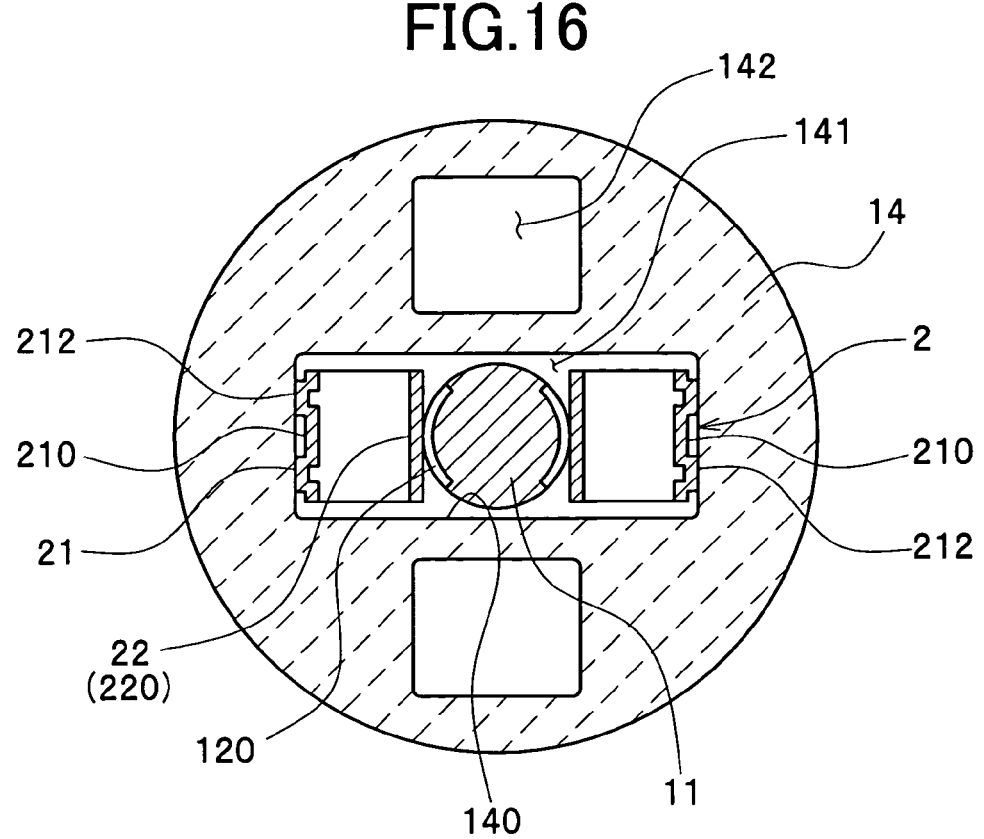
FIG. 16 is a sectional view, taken along the planar direction, showing an atmosphere-side insulator and contact fittings according to a sixth embodiment of the present invention.

Referring to FIG. 16, a sixth embodiment of the present invention will now be described.

As shown in FIG. 16, the present embodiment shows, by way of example, a gas sensor 1 provided with contact fittings 2 each having a base plate 21 on which there are formed two convex portions 212 projecting outward from the rear surface 210. Instead of having these convex portions 212, each contact fitting 2 has no fixing spring members and the atmosphere-side insulator 14 has no groove at its inner wall surface 140.

As shown in FIG. 16, each contact fitting 2 is in contact with the inner wall surface 140 of the atmosphere-side insulator 14 via the two convex portions 212 at two contact points and each contact fitting 2 is in contact with the electrodes 120 of the heater 11 via each electrode contact member 22 at one contact point. It is therefore possible in the same way as the foregoing embodiments that the contact fittings 2 are prevented from vibrating laterally.

Additionally, since each base plate 21 has the convex portions 212, the base plate 21 is enhanced in its strength, whereby deformation, including warpage, of the contact fitting 2 can be restrained. The remaining advantages stated in the first embodiment can also be obtained in the present embodiment.

Seventh Embodiment

Figure 17:
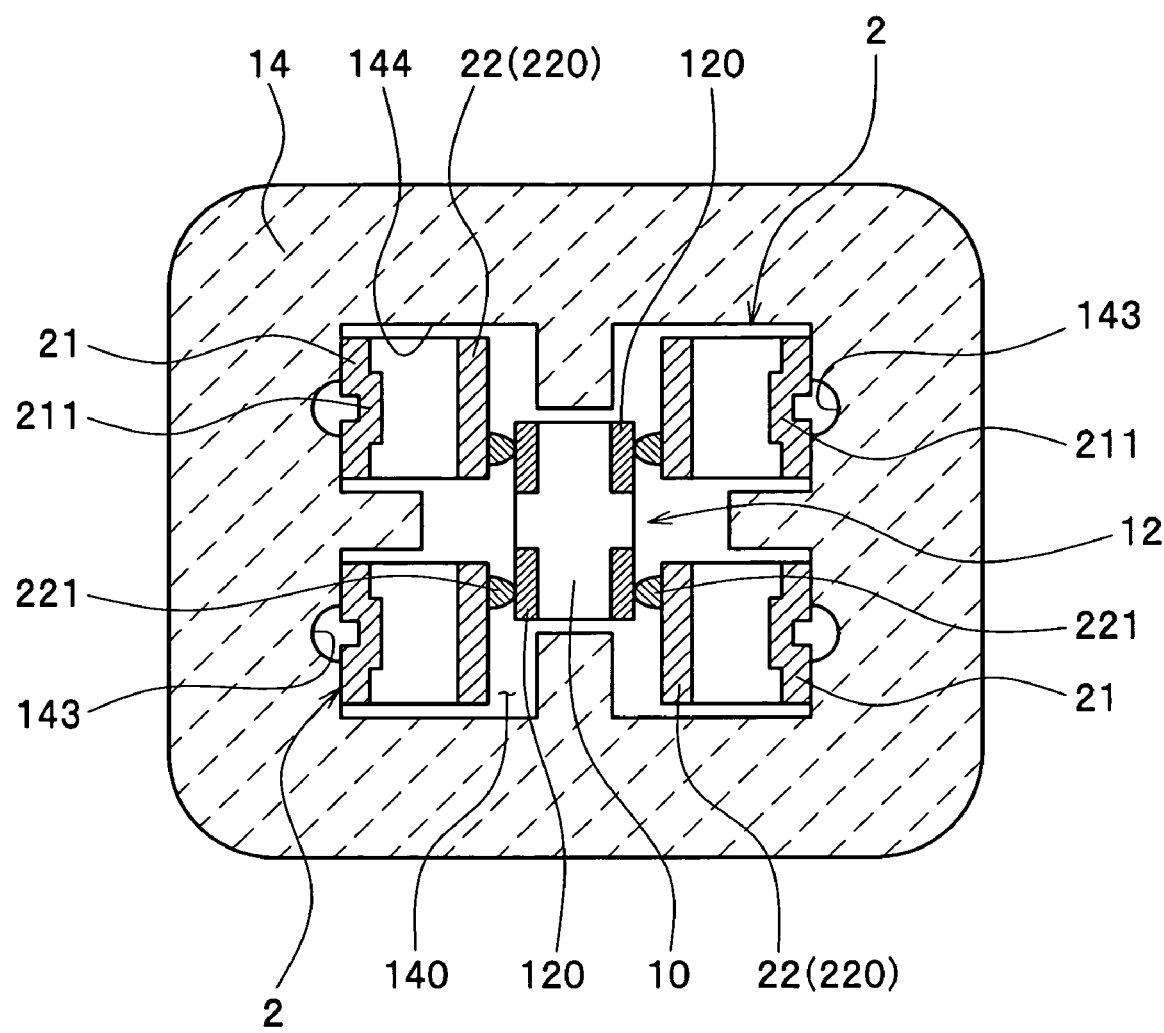
FIG. 17 is a sectional view, taken along the planar direction, showing an atmosphere-side insulator and contact fittings according to a seventh embodiment of the present invention.

Referring to FIG. 17, a seventh embodiment of the present invention will now be described.

As shown in FIG. 17, the present embodiment shows, by way of example, a gas sensor 1 which comprises a sensing element 10 of laminated type. At the base end part 12 of the sensing element 10, a total of four electrodes 120 are disposed for both sensing a gas concentration and heating up the heater.

Thus, corresponding to the four electrodes 120, four contact fittings 2 are disposed. In the atmosphere-side insulator 14, four semi-sectioned through-bores are formed to produce an inner wall surface 140 and to allow lead wires (not shown) to be inserted therethrough for the heater and signal sensing.

As shown in FIG. 17, the atmosphere-side insulator 14 has a total of four grooves 143 recessed on the inner wall surface 140. The grooves 143 are located to face the rear surface 210 of the base plate 21 of each contact fitting 2. In addition, the base plate 21 of each contact fitting 2 has one concave 211 recessed from its rear surface 210.

Further, each contact fitting 2 comprises a projection 221 projecting forward from each electrode contact member 22. This projection 221 is located to contact each corresponding electrode 120. In place of being structured above, each contact fitting 2 has no fixing spring member on both sides of the base plate 21.

In the present embodiment, as shown in FIG. 17, each contact fitting 2 is in contact with the inner wall surface 140 of the atmosphere-side insulator 14 via both plate areas produced by the concave portion 211 on the rear surface 210 at two contact points. Moreover, each contact fitting 2 is in contact with each corresponding electrode 120 of either the sensing element 10 or the heater 11 via each projection 221 at one contact point. In other words, each contact fitting 2 is supported at the three points between the atmosphere-side insulator 14 and the sensing element 10. Therefore, the contact fittings 2 are well prevented from vibrating laterally.

Since each base plate 21 has the concave 211, the base plate 21 is enhanced in its strength, suppressing or eliminating deformation, such as warpage, of the contact fittings 2 caused due to compressing the base end part 12 of the heater 11 or a base end part of the sensing element. The remaining advantages stated in the first embodiment can also be obtained in the present embodiment.

The present invention may be embodied in several other forms without departing from the spirit thereof. The embodiments and modifications described so far are therefore intended to be only illustrative and not restrictive, since the scope of the invention is defined by the appended claims rather than by the description preceding them. All changes that fall within the metes and bounds of the claims, or equivalents of such metes and bounds, are therefore intended to be embraced by the claims.

What is claimed is:

1. A gas sensor comprising:
    a sensing element that detects a concentration of a specific gas component contained in a gas to be measured, the sensing element being elongated to have a longitudinal direction;
    a heater that heats up the sensing element for detection of the concentration;
    an element-holding body that allows the sensing element to be inserted and to be held therein;
    an atmosphere-side insulator formed to have an inner wall surface and disposed to allow the inner wall surface to overlap with a base end part of either the sensing element or the heater in the longitudinal direction;
    a plurality of electrodes disposed on either the sensing element or the heater;
    plurality of contact fittings disposed between the inner wall surface of the atmosphere-side insulator and the base end part of either the sensing element or the heater so as to contact the electrodes for electric conduction to the electrodes, respectively, wherein each of the contact fittings comprises a base plate located to contact the inner wall surface of the atmosphere-side insulator and an electrode contact member located to each of the electrodes; and suppressing means for suppressing the contact fittings from shifting relative to the electrodes in directions crossing the longitudinal direction, the suppressing means being a plurality of elastic members secured to each of the contact fittings and located to press the inner wall surface of the atmosphere-side insulator.

2. The gas sensor of claim 1, wherein the inner wall surface of the atmosphere-side insulator has a groove part recessed from the inner wall surface.

3. The gas sensor of claim 2, wherein the elastic members are spring members formed integrally with the base plate by bending portions of the base plate.

4. The gas sensor of claim 2, wherein the spring members are two in number and located both sides of the electrode contact member along a planar direction of the base plate.

5. The gas sensor of claim 2, wherein the base plate of each of the contact fittings comprises a rear surface that faces the inner wall surface of the atmosphere-side insulator and a concave portion recessed from the inner wall surface.

6. The gas sensor of claim 2, wherein the base plate of each of the contact fittings comprises a rear surface that faces the inner wall surface of the atmosphere-side insulator and a plurality of convex portions projecting toward the inner wall surface.

7. The gas sensor of claim 2, wherein each of the fixing spring members comprises a bent portion formed as a convex oriented toward a base end of the sensing element by bending part of the base plate toward the sensing element and a folded end extending from the bent portion toward the distal end of the sensing element and forcibly pressing the inner wall surface of the atmosphere-side insulator.

8. The gas sensor of claim 7, wherein, when a distance between a distal edge of the base plate, which is on the opposite side to the bent portion, and a tip of the folded end in the longitudinal direction is expressed as "A" and a distance between the distal edge of the base plate and a middle part of the bent portion in the longitudinal direction is expressed as "B," a relationship of "A≧0.05B" is met.

9. The gas sensor of claim 1, wherein the sensing element is a bottomed cylindrical sensing element, the heater is a columnar heater disposed inside the sensing element, the electrodes are disposed on a base end part of the heater, and the contact fittings are made to contact the electrodes on the base end part of the heater.

10. The gas sensor of claim 1, wherein the electrodes comprises a pair of electrodes disposed on the base end part of either the sensing element or the heater and the contact fittings comprises a pair of contact fittings that contact the pair of electrodes, respectively, such that the pair of the contact fittings forcibly pinch the base end part of either the sensing element or the heater.

11. A gas sensor comprising:
a sensing element that detects a concentration of a specific gas component contained in a gas to be measured, the sensing element being elongated to have a longitudinal direction;
a heater that heats up the sensing element for detection of the concentration;
an element-holding body that allows the sensing element to be inserted and to be held therein;
an atmosphere-side insulator formed to have an inner wall surface and disposed to allow the inner wall surface to overlap with a base end part of either the sensing element or the heater in the longitudinal direction;
a plurality of electrodes disposed on either the sensing element or the heater;
a plurality of contact fittings disposed between the inner wall surface of the atmosphere-side insulator and the base end part of either the sensing element or the heater so as to contact the electrodes for electric conduction to the electrodes, respectively, wherein each of the contact fittings comprises a base plate located to contact the inner wall surface of the atmosphere-side insulator and an electrode contact member located to each of the electrodes; and
suppressing means for suppressing the contact fittings from shifting relative to the electrodes in directions crossing the longitudinal direction,
wherein the base plate of each of the contact fittings comprises, as the suppressing means, both a rear surface that faces the inner wall surface of the atmosphere-side insulator and a concave portion recessed from the inner wall surface.

12. The gas sensor of claim 11, wherein the inner wall surface of the atmosphere-side insulator has a groove part recessed from the inner wall surface.

13. The gas sensor of claim 12, wherein the groove part is formed as a groove that runs in the longitudinal direction and is one in number relative to each of the contact fittings.

14. The gas sensor of claim 13, wherein the groove is located at a position opposed to a central position of the rear surface of each of the contact fittings in a planar direction of the base plate.

15. The gas sensor of claim 11, wherein the sensing element is a bottomed cylindrical sensing element, the heater is a columnar heater disposed inside the sensing element, the electrodes are disposed on a base end part of the heater, and the contact fittings are made to contact the electrodes on the base end part of the heater.

16. The gas sensor of claim 11, wherein the electrodes comprises a pair of electrodes disposed on the base end part of either the sensing element or the heater and the contact fittings comprises a pair of contact fittings that contact the pair of electrodes, respectively, such that the pair of the contact fittings forcibly pinch the base end part of either the sensing element or the heater.

17. A gas sensor comprising:
a sensing element that detects a concentration of a specific gas component contained in a gas to be measured, the sensing element being elongated to have a longitudinal direction;
a heater that heats up the sensing element for detection of the concentration;
an element-holding body that allows the sensing element to be inserted and to be held therein;
an atmosphere-side insulator formed to have an inner wall surface and disposed to allow the inner wall surface to overlap with a base end part of either the sensing element or the heater in the longitudinal direction;
a plurality of electrodes disposed on either the sensing element or the heater;
a plurality of contact fittings disposed between the inner wall surface of the atmosphere-side insulator and the base end part of either the sensing element or the heater so as to contact the electrodes for electric conduction to the electrodes, respectively, wherein each of the contact fittings comprises a base plate located to contact the inner wall surface of the atmosphere-side insulator and an electrode contact member located to each of the electrodes; and
suppressing means for suppressing the contact fittings from shifting relative to the electrodes in directions crossing the longitudinal direction, wherein the base plate of each of the contact fittings comprises, as the suppressing means, both a rear surface that faces the inner wall surface of the atmosphere-side insulator and a plurality of convex portions projecting toward the inner wall surface.

18. The gas sensor of claim 17, wherein the sensing element is a bottomed cylindrical sensing element, the heater is a columnar heater disposed inside the sensing element, the electrodes are disposed on a base end part of the heater, and the contact fittings are made to contact the electrodes on the base end part of the heater.

19. The gas sensor of claim 17, wherein the electrodes comprises a pair of electrodes disposed on the base end part of either the sensing element or the heater and the contact fittings comprises a pair of contact fittings that contact the pair of electrodes, respectively, such that the pair of the contact fittings forcibly pinch the base end part of either the sensing element or the heater.

20. A gas sensor comprising:
   a sensing element that detects a concentration of a specific gas component contained in a gas to be measured, the sensing element being elongated to have a longitudinal direction;
   a heater that heats up the sensing element for detection of the concentration;
   an element-holding body that allows the sensing element to be inserted and to be held therein;
   an atmosphere-side insulator formed to have an inner wall surface and disposed to allow the inner wall surface to overlap with a base end part of either the sensing element or the heater in the longitudinal direction;
   a plurality of electrodes disposed on either the sensing element or the heater;
   a plurality of contact fittings disposed between the inner wall surface of the atmosphere-side insulator and the base end part of either the sensing element or the heater so as to contact the electrodes for electric conduction to the electrodes, respectively, wherein each of the contact fittings comprises a base plate located to contact the inner wall surface of the atmosphere-side insulator and an electrode contact member located to each of the electrodes; and
   suppressing means for suppressing the contact fittings from shifting relative to the electrodes in directions crossing the longitudinal direction,
   wherein the inner wall surface of the atmosphere-side insulator has, as the suppressing means, a groove part recessed therefrom.

21. The gas sensor of claim 20, wherein the sensing element is a bottomed cylindrical sensing element, the heater is a columnar heater disposed inside the sensing element, the electrodes are disposed on a base end part of the heater, and the contact fittings are made to contact the electrodes on the base end part of the heater.

22. The gas sensor of claim 20, wherein the electrodes comprises a pair of electrodes disposed on the base end part of either the sensing element or the heater and the contact fittings comprises a pair of contact fittings that contact the pair of electrodes, respectively, such that the pair of the contact fittings forcibly pinch the base end part of either the sensing element or the heater.

* * * * *